US005653242A

United States Patent [19]

Brockelsby

[11] Patent Number: 5,653,242

[45] Date of Patent: Aug. 5, 1997

[54] TRANSMITTER IMPLANT TO INDICATE PARTURITION

[75] Inventor: William Keith Brockelsby, Edmonton, Canada

[73] Assignee: Ultratec (1995) Inc., High Prairie, Canada

[21] Appl. No.: 430,842

[22] Filed: Apr. 28, 1995

[51] Int. Cl.$^6$ .................................................. A61B 10/00

[52] U.S. Cl. .................................................. 128/738

[58] Field of Search ............................ 128/738, 775, 128/778; 340/573

[56] References Cited

U.S. PATENT DOCUMENTS

| | | | |
|---|---|---|---|
| 3,583,389 | 6/1971 | Harvey | 128/2 R |
| 4,028,687 | 6/1977 | Hamaguchi et al. | 340/201 R |
| 4,217,575 | 8/1980 | Lorette | 128/775 |
| 4,232,686 | 11/1980 | Kammlade, Jr. | 128/775 |
| 4,264,900 | 4/1981 | Charlier | 340/573 |
| 4,319,583 | 3/1982 | Ingle | 128/775 |
| 4,503,808 | 3/1985 | McAlister | 119/1 |
| 4,651,137 | 3/1987 | Zartman | 340/573 |
| 4,784,155 | 11/1988 | Mills | 128/734 |
| 4,854,328 | 8/1989 | Pollack | 128/736 |
| 4,936,316 | 6/1990 | Jewett | 128/775 |
| 4,994,665 | 2/1991 | Wernsing | 250/221 |
| 5,111,799 | 5/1992 | Senger et al. | 128/738 |

FOREIGN PATENT DOCUMENTS

| | | | |
|---|---|---|---|
| 2 582 507 | 12/1986 | France | A61D 1/08 |
| 1690083 | 4/1971 | Germany . | |
| 8802588 | 5/1990 | Netherlands . | |

*Primary Examiner*—Max Hindenburg
*Attorney, Agent, or Firm*—Anthony R. Lambert

[57] ABSTRACT

A method of triggering a transmitter implant during parturition is described. Firstly, provide a transmitter implant that is housed in a flexible housing and is activated to transmit a signal upon the housing being flexed. Secondly, implant the transmitter implant in a vulva lip of an animal where it will be unavoidably flexed during parturition.

1 Claim, 2 Drawing Sheets

FIG. 1.
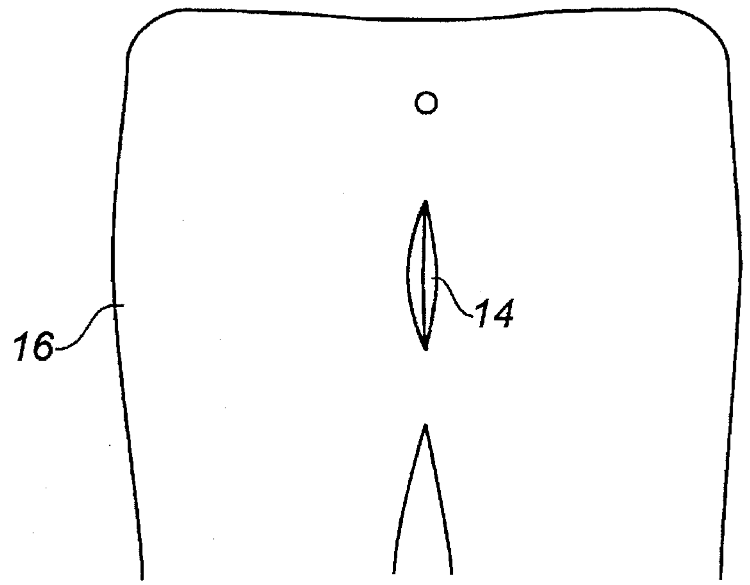
FIG. 2.
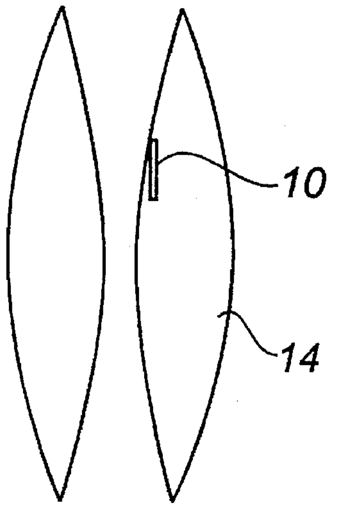
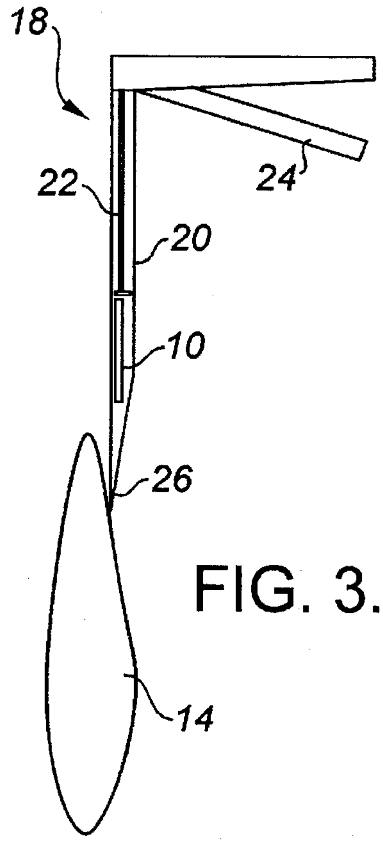
FIG. 3.

TRANSMITTER IMPLANT TO INDICATE PARTURITION

FIELD OF THE INVENTION

The present invention relates to remote parturition monitoring systems and, in particular to a method of triggering a transmitter implant during parturition and a transmitter implant that operates in accordance with the teachings of the method.

BACKGROUND OF THE INVENTION

U.S. Pat. No. 4,232,686 which issued to Kammlade Jr. in 1980 and U.S. Pat. No. 4,319,583 which issued to Ingle in 1982 both disclose remote parturition monitoring systems for use with livestock. The transmitter disclosed in the Kammlade reference consists of a rupturable assembly which is mounted externally across the vaginal orifice of the animal. The transmitter disclosed in the Ingle reference consists of a magnet positioned on one side of an animal's vulva and a switch mechanism positioned on the other side of an animal's vulva. When the magnet is moved out of the field sensing area of the switch mechanism during parturition, the switch mechanism activates a transmitter.

U.S. Pat. No. 4,936,316 which issued to Jewett in 1990 describes problems of false triggering which have been encountered in prior art transmitters, such as those taught by Kammlade and Ingle. With the Kammlade reference problems of false triggering are described as arising if great case is not taken to ensure correct installation. With the Ingle reference, false triggering occurs from any movements of the animal which displace the magnet outside of a preset range. False triggering can occur when the animals rub against fixed objects. Apparently, such rubbing is common as the animals attempt to relieve the sensory perceptions associated with the presence of the device. The solution to false triggering, as taught by Jewett, consists of placing a magnet in a housing positioned on one side of the animals vulva and attaching a thong between the magnet and the other side of the animals vulva. Upon parturition occurring, the magnet is pulled from the housing by means of the thong, thereby triggering a switch that activates the transmitter.

SUMMARY OF THE INVENTION

What is required is an alternative method of triggering a transmitter implant during parturition that will not be as prone to false triggering.

According to one aspect of the present invention there is provided a method of triggering a transmitter implant during parturition. Firstly, provide a transmitter implant that is housed in a flexible housing and is activated to transmit a signal upon the housing being flexed. Secondly, implant the transmitter implant in a vulva lip of an animal where it will be unavoidably flexed during parturition.

With the method, as described, it is extremely unlikely that a false triggering will occur as a result of the animal rubbing against a fixed object or engaging in other activities. The transmitter is triggered only when a flexing occurs, and such flexing can only occur when the vulva expands during parturition. Once the teachings of the present invention are understood, it will be appreciated that the transmitter implant can take a variety of forms.

According to another aspect of the present invention there is provided a transmitter implant. The transmitter implant includes a flexible elongate housing and a transmitter disposed within the flexible housing. A power cell is also disposed within the flexible housing. A conductive power circuit is connected to the transmitter and spaced from the power cell. Flexing of the housing brings the power cell into contact with the conductive power circuit thereby supplying power to the transmitter.

BRIEF DESCRIPTION OF THE DRAWINGS

These and other features of the invention will become more apparent from the following description in which reference is made to the appended drawings, wherein:

FIG. 1 is an end elevation view of an animal having a transmitter implant in accordance with the teachings of the present method.

FIG. 2 is a detailed view of the animal having the transmitter implant illustrated in FIG. 1.

FIG. 3 is a side elevation view, partially in section, of implantation in an animal of the transmitter implant in accordance with the teaching of the method illustrated in FIG. 1.

DETAILED DESCRIPTION OF THE PREFERRED EMBODIMENT

The preferred method of triggering a transmitter implant during parturition will now be described with reference to FIGS. 1 through 6.

Figure 4:
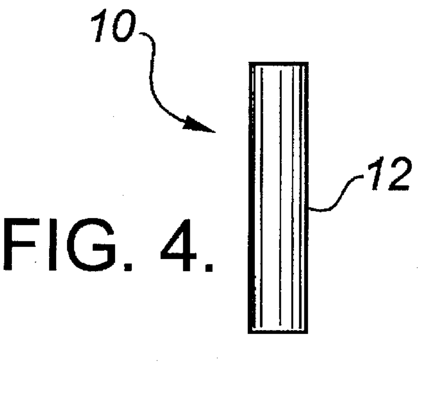
FIG. 4 is a side elevation view (actual size) of a transmitter implant constructed in accordance with the teachings of the present invention.
Figure 5:
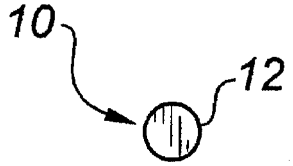
FIG. 5 is a top plan view (actual size) of the transmitter implant illustrated in FIG. 3.

The preferred method consists of the following steps. Firstly, provide a transmitter implant 10 that is housed in a flexible housing 12 and is activated to transmit a signal upon the housing being flexed. The dimensions of flexible housing 12 of transmitter implant 12 are illustrated in FIGS. 4 and 5. The flexing of flexible housing 12 that results in the transmission of a signal, is an axial flexing in which flexible housing 12 assumes an arcuate shape. Secondly, implant transmitter implant 10 in a vulva lip 14 of an animal 16 where it will be unavoidably flexed during parturition. One method of implantation is illustrated in FIG. 3, utilizing a plunger style of implant tool, generally indicated by reference numeral 18. Implant tool 18 has a tubular barrel 20 in which is positioned an axially movable plunger 22. Plunger 22 moves axially along barrel 20 upon a force being exerted upon lever 24. Barrel 20 ends in a needle tip 26. In order to implant transmitter implant 10, transmitter implant 10 is positioned within barrel 20. The vulva lip 14 of animal 16 is opened with one hand while the other hand positions implant tool 18 in a substantially vertical position. Needle tip 26 is then pushed into vulva lip 14. Plunger 22 is then moved by means of lever 24 to push transmitter implant 10 into an implanted position within an upper portion of vulva lip 14. The positioning is illustrated in FIGS. 1 and 2.

With the method, as described, it is extremely unlikely that a false triggering will occur as a result of the animal rubbing against a fixed object or engaging in other activities. Transmitter implant 10 transmits only when an axial flexing of flexible housing 12 occurs. It is unlikely that such flexing will only occur, except when vulva lip 14 is forced to expand during parturition.

Figure 6:
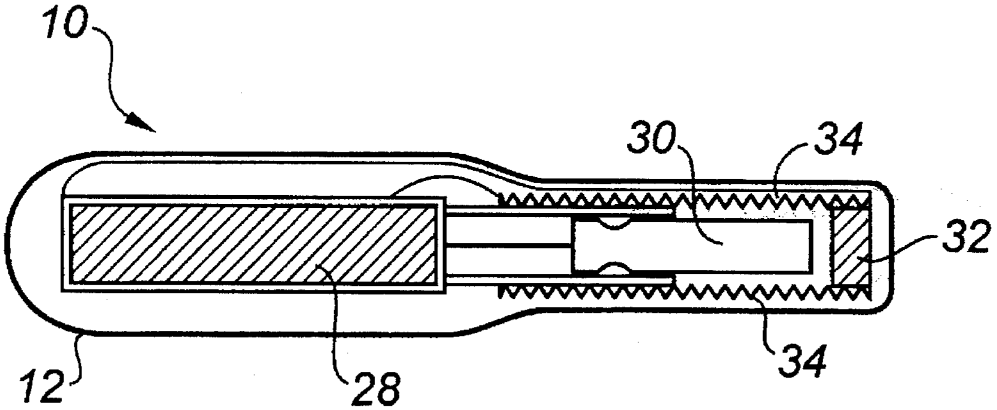
FIG. 6 is a side elevation view in longitudinal section the transmitter implant illustrated in FIG. 3.

The internal workings of transmitter implant 10 are illustrated in FIG. 6. As previously described, a flexible elongate housing 12 is provided. Flexible housing 12 is made out of or coated with a tissue tolerant plastic. A transmitter 28 and a power cell 30 are disposed within flexible housing 12. A conductive power circuit 32 is connected to transmitter 28 and spaced from power cell 30. Conductive power circuit 32 is configured so that an axial flexing of flexible housing 12 will bring power cell 30 into contact with conductive power circuit 32 thereby supplying power to transmitter 28. FIG. 6 illustrates a preferred configuration for conductive power circuit 32. Conductive power circuit 32 includes flexible springs 34. When an axial flexing or bending of flexible housing 12 occurs springs 34 forming part of conductive power circuit 32 are brought into contact with power cell 30, thereby providing power to transmitter 28.

When the water bag, feet, head or body of the fetus passes through, it causes stretching and curving of vulva lip 14. Flexible housing 12 follows the curving of vulva lip 14. This bending activates transmitter 28, as previously described. Once installed, transmitter implant 10 can remain operation for 5 to 10 years, depending upon the demands made upon it due to birthing difficulties.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A transmitter implant, comprising:

a flexible elongate housing, the housing being capable of omni-directional axial flexing;

a transmitter disposed within the flexible housing;

a power cell disposed within the flexible housing, the power cell being axially spaced from the transmitter; and a conductive power circuit including a plurality of springs connected to the transmitter and extending in parallel spaced relation to the power cell, such that flexing of the housing brings the power cell into contact with the springs of the conductive power circuit thereby supplying power to the transmitter.

* * * * *